US009211188B2

(12) United States Patent
McMinn

(10) Patent No.: US 9,211,188 B2
(45) Date of Patent: Dec. 15, 2015

(54) FEMORAL HEAD PROSTHESIS

(76) Inventor: Derek James Wallace McMinn, West Midlands (GB)

( * ) Notice: Subject to any disclaimer, the term of this patent is extended or adjusted under 35 U.S.C. 154(b) by 0 days.

(21) Appl. No.: 14/127,020

(22) PCT Filed: Jul. 13, 2012

(86) PCT No.: PCT/GB2012/051675
§ 371 (c)(1),
(2), (4) Date: Feb. 12, 2014

(87) PCT Pub. No.: WO2013/011290
PCT Pub. Date: Jan. 24, 2013

(65) Prior Publication Data
US 2014/0207246 A1  Jul. 24, 2014

(30) Foreign Application Priority Data

Jul. 15, 2011  (GB) .................................. 1112287.6
Apr. 2, 2012  (GB) .................................. 1205877.2

(51) Int. Cl.
*A61F 2/36* (2006.01)
*A61F 2/30* (2006.01)
(52) U.S. Cl.
CPC ............. *A61F 2/3609* (2013.01); *A61F 2/3607* (2013.01); *A61F 2002/30112* (2013.01);
(Continued)
(58) Field of Classification Search
CPC ....... A61F 2/3607; A61F 2/3609; A61F 2/36; A61F 2/3601
USPC ...................... 623/19.11–19.14, 22.11, 22.15, 623/22.17–22.2, 22.4–22.46, 23.11–23.15, 623/23.18, 23.25, 23.42–23.44
See application file for complete search history.

(56) References Cited

U.S. PATENT DOCUMENTS 2,718,228 A * 9/1955 Van Steenbrugghe ..... 623/23.14
3,979,778 A * 9/1976 Stroot ........................ 623/19.12
(Continued)

FOREIGN PATENT DOCUMENTS

DE       9103574 U1   4/1992
EP       1228739 A2   8/2002
(Continued)

OTHER PUBLICATIONS

International Search Report and Written Opinion for International Application No. PCT/GB2012/051675 issued Oct. 2, 2012 and mailed Oct. 10, 2012.
(Continued)

*Primary Examiner* — Marcia Watkins
(74) *Attorney, Agent, or Firm* — Morgan, Lewis & Bockius LLP

(57) ABSTRACT

A femoral head prosthesis (110) comprises an articulating surface (112) which is more than hemi-spherical; an internal recess (114) having a longitudinal axis defining a pole P of the articulating surface (112), the longitudinal axis passing through the center of curvature of the articulating surface (112); a first edge (116) which constitutes a posterior edge in use, and a second edge (118) which constitutes an anterior edge and/or an antero-inferior edge in use. The first edge (116) is further from the pole P than the second edge (118). Also provided is a femoral prosthesis comprising a femoral head, and a femoral implant comprising a femoral stem and a femoral head. The prostheses and implants of the invention find use in total hip replacements.

15 Claims, 5 Drawing Sheets

(52) U.S. Cl.
CPC .............. *A61F2002/30332* (2013.01); *A61F 2002/30367* (2013.01); *A61F 2002/30474* (2013.01); *A61F 2002/30604* (2013.01); *A61F 2002/30688* (2013.01)

(56) References Cited

U.S. PATENT DOCUMENTS

| | | | |
|---|---|---|---|
| 4,532,661 A * | 8/1985 | Halpern | 623/23.14 |
| 5,480,451 A | 1/1996 | Grundei et al. | |
| 5,735,905 A * | 4/1998 | Parr | 623/23.11 |
| 8,764,845 B2 * | 7/2014 | Brooks et al. | 623/23.11 |
| 2005/0060040 A1 | 3/2005 | Auxepaules et al. | |
| 2005/0065612 A1 * | 3/2005 | Winslow | 623/19.14 |
| 2006/0036328 A1 * | 2/2006 | Parrott et al. | 623/19.14 |
| 2007/0106389 A1 | 5/2007 | Croxton et al. | |
| 2008/0221700 A1 * | 9/2008 | Howald et al. | 623/23.12 |
| 2009/0192622 A1 * | 7/2009 | Long et al. | 623/19.14 |
| 2014/0128988 A1 | 5/2014 | Muratoglu et al. | |

FOREIGN PATENT DOCUMENTS

| | | |
|---|---|---|
| FR | 2631543 A1 | 11/1989 |
| WO | 2008/117053 A1 | 10/2008 |
| WO | WO2014052768 | 4/2014 |

OTHER PUBLICATIONS

GB Search Report for Application No. GB1112287.6 dated Oct. 28, 2011.
Examination Report Received for Chinese Patent Application No. 201280035184.4, mailed on Apr. 17, 2015, 6 pages. (3 pages of English Translation and 6 pages of Official Copy).

* cited by examiner

FEMORAL HEAD PROSTHESIS

RELATED APPLICATIONS

This application is a U.S. National Phase Application of PCT/GB2012/051675, filed Jul. 13, 2012, which claims priority to and the benefit of United Kingdom Patent Application No. 1112287.6, filed on Jul. 15, 2011, and United Kingdom Patent Application No. 1205877.2, filed Apr. 2, 2012, all of which are incorporated herein by reference.

FIELD OF THE INVENTION

The present invention relates to a femoral head prosthesis. Particularly, but not exclusively, the invention relates to a large femoral head prosthesis for use in total hip replacements.

BACKGROUND TO THE INVENTION

Large femoral heads are increasingly being used in total hip replacement procedures. Some advantages of using a large femoral head are a reduced dislocation rate and reduced impingement between a femoral neck of a hip replacement prosthesis and a corresponding acetabular cup edge.

However, a disadvantage of the use of large femoral heads is intermittent groin pain, thought to be due to interference with a free excursion of a psoas tendon. As illustrated in FIG. 1, a psoas muscle 10 takes its origin on the lumbar spine 12, a tendon 14 of psoas passes over the front of the bony pelvis 16, the hip joint 18, the femoral head 20 and the antero-inferior femoral neck 22 before insertion into the lesser trochanter 24. The action of the psoas muscle 10 flexes the hip joint 18.

Small femoral heads that have hitherto been used as prosthetic heads on a total hip replacement femoral stem have been of a mono-block construct. Large metal femoral head prostheses are commonly not mono-block constructs as designers and manufacturers seek to reduce the weight inevitable with the use of solid metal components. Commonly, large femoral head components are partially hollowed out to reduce weight with a tapering neck of a femoral stem engaging in a correspondingly tapered female recess in the femoral head component. Even more commonly, a sleeve is employed over the neck to reduce the inventory of femoral head components needed for a hip replacement operation (with multiple lengths and, in certain designs, offsets being available through the use of different sleeves).

FIG. 2 illustrates a known femoral implant design 30 comprising a femoral head 32, a conical sleeve 34, and a femoral stem 36. The femoral head 32 is constituted by a partially hollowed out part-spherical metallic component with an inwardly tapering channel 38 provided approximately at its centre, for receipt of the sleeve 34 therewithin. The femoral stem 36 comprises a elongated portion 40, which generally tapers away from the femoral head 32 and terminates in a rounded tip 42, an intermediate portion 44, having approximately straight parallel sides 46, and a neck portion 48, which extends in an offset antero-inferior direction and terminates in a conical taper 50 which is received within the sleeve 34. As illustrated, the femoral head 32 comprises a relatively thin depending edge or skirt 52 which surrounds the interconnecting channel 38, sleeve 34 and conical taper 50 but which is spaced therefrom to accommodate a portion of a patient's resected femoral neck to secure the implant on the patient's femur.

It has, however, been found that groin pain is commonly associated with the use of such hollowed-out femoral heads, like that illustrated in FIG. 2.

It is therefore an aim of the present invention to provide an improved femoral head prosthesis.

SUMMARY OF THE INVENTION

According to a first aspect of the present invention there is provided a femoral head prosthesis comprising an articulating surface which is more than hemi-spherical; an internal recess having a longitudinal axis defining a pole of the articulating surface, the longitudinal axis passing through the centre of curvature of the articulating surface; a first edge which constitutes a posterior edge in use, and a second edge which constitutes an anterior edge and/or an antero-inferior edge in use; and wherein the first edge is further from the pole than the second edge.

It will be understood that the femoral head prosthesis of the first aspect of the invention may be configured for use with a femoral stem prosthesis having a neck portion which is either configured for direct (press-fit) insertion into the internal recess or for (press-fit) insertion into an intervening sleeve, which in turn is (press-fit) inserted into the internal recess. Thus, the femoral head of the first aspect of the invention may form a part of a multi-part femoral implant in which the head is fixedly provided on a femoral stem, with or without the inclusion of an intervening sleeve and wherein the sleeve may or may not be configured for offset engagement with the stem.

According to a second aspect of the present invention there is provided a femoral implant comprising a femoral stem and a femoral head; the femoral head comprising an articulating surface which is more than hemi-spherical; the femoral stem comprising a neck having a longitudinal axis defining a pole of the articulating surface of the femoral head, the longitudinal axis passing through the centre of curvature of the articulating surface; the femoral head having a first edge which constitutes a posterior edge in use, and a second edge which constitutes an anterior edge and/or an antero-inferior edge in use; and wherein the first edge is further from the pole than the second edge.

It will be understood that the femoral implant of the second aspect of the invention may be configured as a one-piece component having an integral femoral head and femoral stem.

Embodiments of the first two aspects of the invention therefore provide a femoral head (either alone or integral with a femoral stem) having a low anterior/antero-inferior profile. The femoral head is therefore asymmetrical in an anterior to posterior direction. The Applicant believes that such a design may help to eliminate the groin pain encountered with prior art components since he believes such pain to be caused by the sharp and bulky depending edge of those femoral heads interfering with the excursion of the psoas tendon anteriorly and/or antero-inferiorly. By reducing the extent of the femoral head anteriorly and/or antero-inferiorly, in accordance with the present invention, it is therefore hoped that the advantages of using large femoral heads can be realised without an associated risk of groin pain.

The prior art of FR2631543 and U.S. Pat. No. 5,480,451 both relate to femoral heads which differ from the those of the present invention since they each require a recess having a longitudinal axis which is offset from the central axis of the head such that they do not feature a longitudinal axis which passes through the centre of curvature of the articulating surface to thereby define the pole in relation to which the posterior and anterior edges of the present invention are defined. Furthermore, it would not be obvious to adapt these prior art devices in order to arrive at the claimed invention since they each require this angulation of the recess in order to provide a desired angle between the long axis of the femoral stem and the head so as to enable the anteversion/retroversion of the head to be altered. Therefore, these documents aim to address an entirely different problem to that of the present invention. In addition, it is noted that rotation of the prior art heads with respect to a femoral stem would necessarily result in a change of the position of the head centre with respect to the stem but, in embodiments of the present invention, rotation of the head does not alter the position of the head centre with respect to the stem since the longitudinal axis passes through the centre.

It will be noted that in a posterior direction, the femoral head may protrude to the same (or a similar) degree as in a traditional femoral head design. This is important because, due to femoral neck anteversion and acetabular component anteversion, a more complete femoral head prosthesis is required posteriorly for satisfactory articulation between the posterior head and acetabular components. Thus, the present invention allows for reduced bulk in regions where it is not essential whilst maintaining material in other regions where it is required for satisfactory load transfer and range of movement.

An anterior-posterior plane may be defined which is perpendicular to the axis of the pole and passes through the centre of curvature of the articulating surface. The second edge may begin (i.e. has an outer end) at (approximately) an intersection between the anterior-posterior plane and the articulating surface (i.e. at a position which is approximately 90 degrees from the pole). Diametrically opposite to said intersection, the articulating surface may cross the anterior-posterior plane such that the first edge begins (i.e. has an outer end) at a position which is more than 90 degrees from the pole (for example, 100, 110, 120 or 130 degrees).

The second edge may comprise an arcuate portion having a radius of curvature which is less than that of the articulating surface. The second edge may comprise an outer end wherein a tangent to the arcuate portion is perpendicular to the anterior-posterior plane and/or may comprise an inner end wherein a tangent to the arcuate portion is parallel to the anterior-posterior plane. This feature therefore eliminates the sharp edge commonly provided on a femoral head prosthesis in an anterior and/or antero-inferior location.

The first edge may be approximately parallel to the anterior-posterior plane.

The first and second edges may be joined by at least one intermediate edge. In a particular embodiment, the first and second edges may be joined by two diametrically opposed intermediate edges. The intermediate edges may provide a smoothly curved step from the (lower) first edge to the (higher) second edge.

The recess of the femoral head may be tapered inwardly towards the pole. Similarly, the neck of the femoral stem may be tapered inwardly towards the pole.

The femoral head may comprise only a single internal recess which is configured for receipt of a sleeve and/or a femoral neck. The recess may be of an inwardly tapering frusto-conical shape. The recess may terminate at an inner end of the second edge and an inner end of the first edge. It will therefore be understood that the recess of the present invention may have an outer diameter which is proportionally larger than that of prior art components where the recess is provided within a separate channel which is set back from the depending skirt of the femoral head. This feature therefore not only helps to reduce the overall bulk and weight of the component but also eliminates the need for sharp edges.

The femoral head may be symmetrical about a plane which is collinear with the pole and which extends along an anterior-posterior direction.

The femoral head may have an outer diameter in the range of 38 mm to 58 mm. A kit comprising a set of femoral heads having outer diameters increasing in 2 mm increments within this range, may be provided.

The femoral head may comprise one or more of metal, ceramic and polymeric materials.

According to a third aspect of the invention there is provided a femoral prosthesis comprising the head according to the first aspect of the invention and one or more of a femoral stem prosthesis and a sleeve for a femoral neck.

It should be noted that an aim of the present invention is to employ a large femoral head (having a large outer diameter) on a relatively narrow femoral neck.

The sleeve may be configured such that, when inserted into the internal recess of the femoral head, a base of the sleeve is level with an inner end of the second edge. This further helps to eliminate sharp edges in the design, which could catch on the psoas tendon.

The sleeve may comprise a generally frusto-conical annulus having an inner surface configured for mating with a co-operating end of a femoral neck prosthesis.

In certain embodiments, the inner surface of the sleeve may be offset with respect to the centre of the sleeve so that the central axis of the sleeve is not coincident with the central axis of the co-operating end of the femoral neck.

An inventory of different sleeves may be provided in order to adjust the position (e.g. the height) of the articulating surface with respect to the femoral neck or stem. In order to ensure that the base of each sleeve remains level with an inner end of the second edge in each case, the inner surface of the sleeve may be altered so that it engages with the end of the femoral neck at varying positions therewithin. For example, to obtain an increase in length, a sleeve would be chosen with a relatively narrow opening so that the neck would engage with the inner surface at a position close to the base of the sleeve and to obtain a shortening in length, a sleeve would be chosen with a relatively wide opening so that the neck would engage with the inner surface at a position close to a top of the sleeve.

According to a fourth aspect of the present invention there is provided a hip joint prosthesis comprising a femoral head according to the first aspect of the present invention or a femoral implant according to the second aspect of the present invention, and an acetabular cup configured to receive said femoral head.

BRIEF DESCRIPTION OF THE DRAWINGS

Specific embodiments of the present invention are described in more detail below with reference to the accompanying drawings, in which.

DETAILED DESCRIPTION OF CERTAIN EMBODIMENTS

Figure 3A:
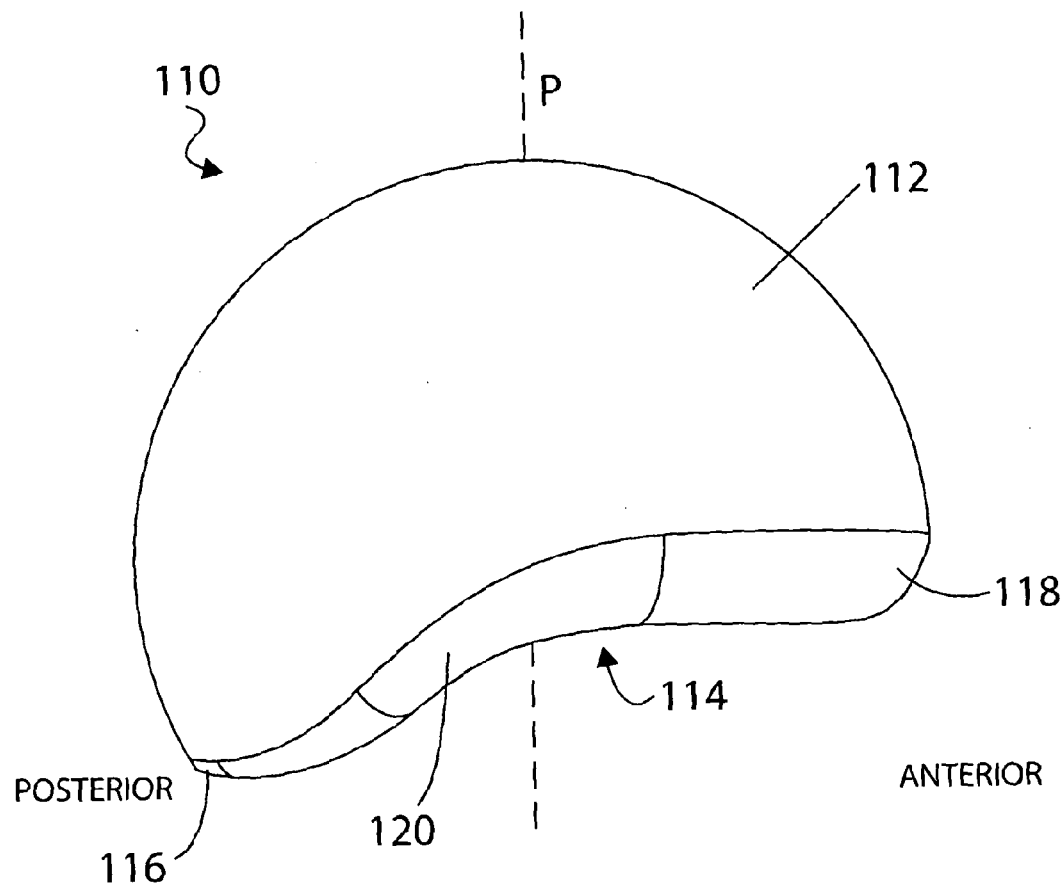
FIG. 3A shows a side view of a femoral head according to an embodiment of the present invention.
Figure 3B:
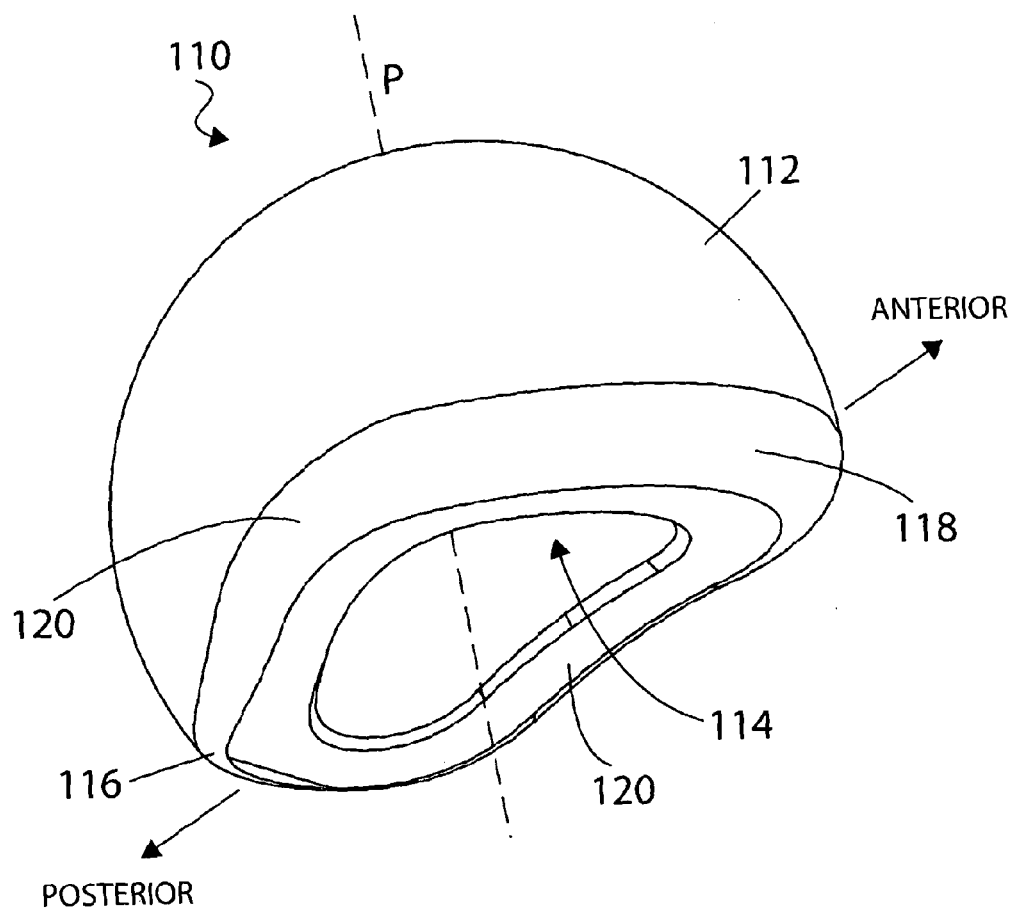
FIG. 3B shows an underside perspective view of the femoral head of FIG. 3A.

With reference to FIGS. 3A and 3B, there is illustrated a metal femoral head 110 according to a first embodiment of the present invention. The femoral head 110 comprises an articulating surface 112 which is more than hemi-spherical and an internal recess 114 having a longitudinal axis defining a pole P of the articulating surface 112. A first edge 116 is provided which constitutes a posterior edge in use, and a second edge 118 is provided which constitutes an anterior edge and an antero-inferior edge in use. Importantly, the first edge 116 is further from the pole P than the second edge 118.

The first and second edges 116, 118 are joined on both sides of the articulating surface 112, by an intermediate edge 120. As illustrated, the intermediate edges 120 provide a smoothly curved step from the lower first edge 116 to the higher second edge 118.

It will be noted that the femoral head 110 is symmetrical about a first plane which is collinear with the pole P and which extends along an anterior-posterior direction and is asymmetrical about a second plane which is also collinear with the pole P but which is orthogonal with the first plane.

As best shown in FIG. 3A, significantly less bulk metal is provided on the anterior and antero-inferior edge 118 of the femoral head 110 than on the posterior edge 116. Consequently, there is a reduced risk of the anterior or antero-inferior edge 118 catching on the psoas tendon 14 and causing groin pain while, at the same time, there is provided an adequate articulating surface at the posterior edge 116 to allow for femoral neck anteversion and/or acetabular component anteversion.

Figure 1:
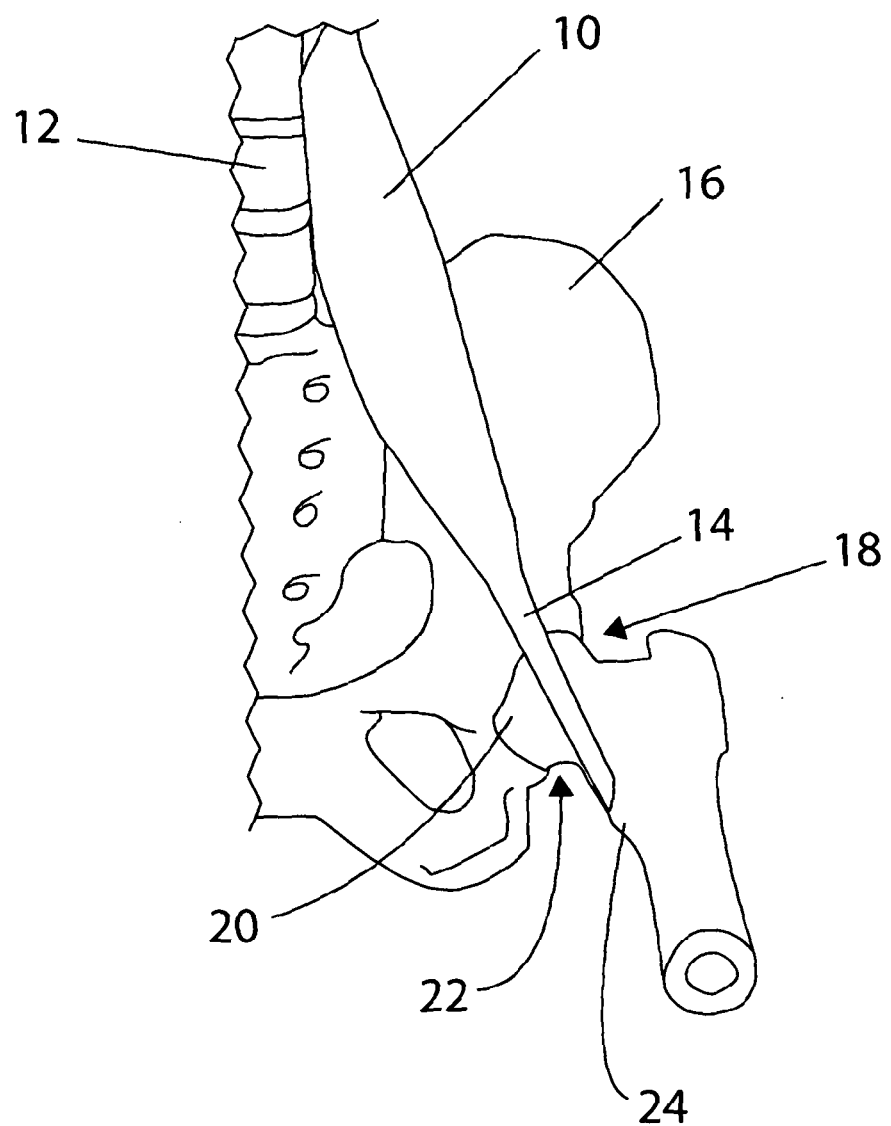
FIG. 1 shows the anatomical configuration of the psoas muscle, a psoas tendon, the hip joint, and the femoral head.
Figure 2:
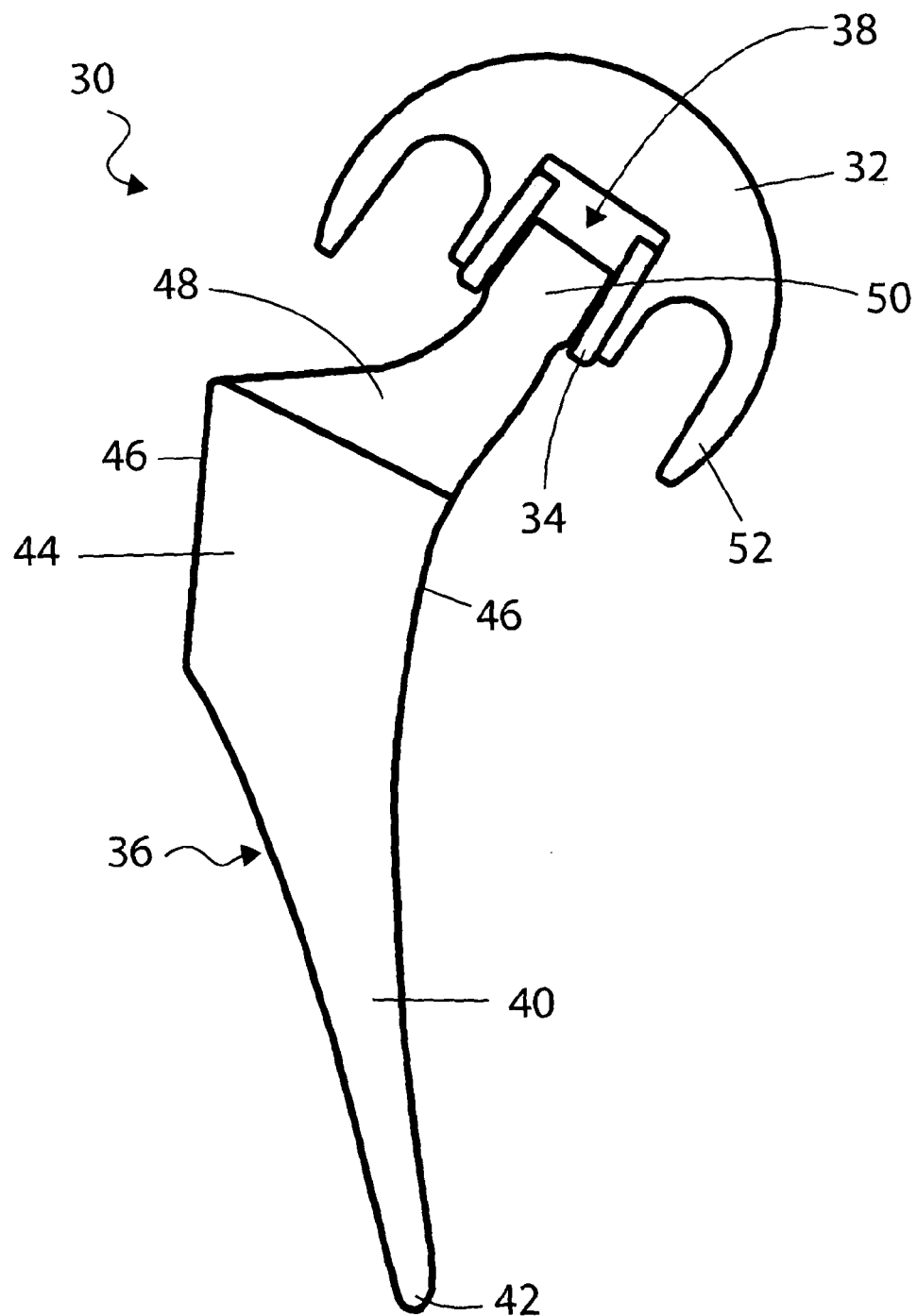
FIG. 2 shows a known femoral implant design.
Figure 4:
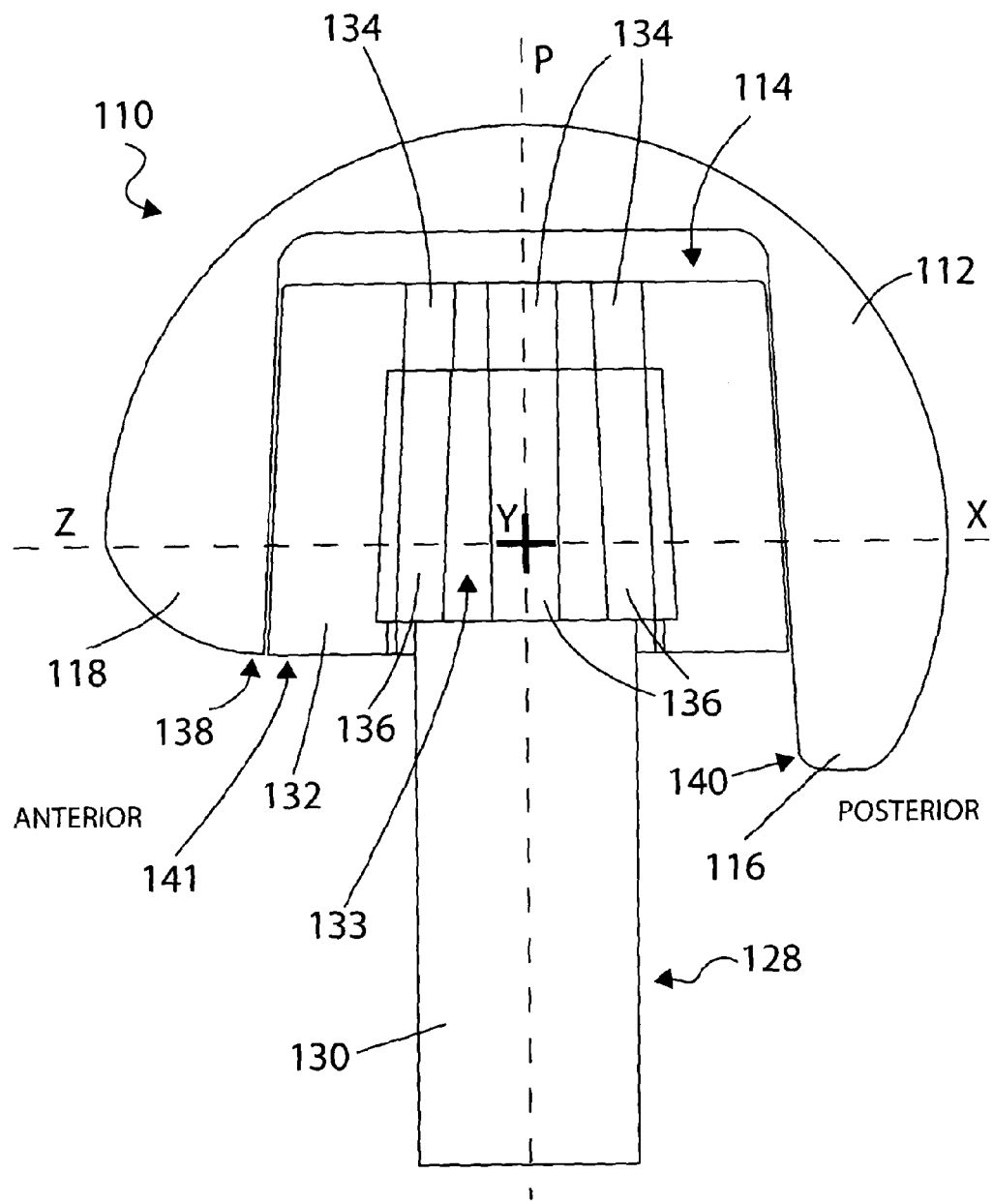
FIG. 4 shows a side cross-sectional view of the femoral head of FIG. 3A when rotated 180 degrees about a vertical axis and when mounted on a representative femoral neck and sleeve.

As shown in FIG. 4, the femoral head 110 of FIGS. 3A and 3B is configured for use with a femoral stem prosthesis 128 (which is similar to that shown in FIG. 2 although it is only shown in part in FIG. 4), and which has a neck portion 130 which is configured for insertion into a sleeve 132, which in turn is inserted into the internal recess 114.

In this particular embodiment, the recess 114 is inwardly tapering towards the pole P and is frusto-conical in shape. Similarly, the sleeve 132 comprises a generally frusto-conical annulus and the neck 130 comprises a generally frusto-conical end 133. However, the sleeve 132 is also provided with a series of spaced apart flat surfaces 134 along its inner surface in order to mate with corresponding flat surfaces 136 provided around the end 133 of the neck 130 to prevent rotation of the sleeve 134 with respect to the neck 130.

As shown in FIG. 4, the recess 114 terminates at an inner end 138 of the second edge 118 and an inner end 140 of the first edge 116. Accordingly, the recess 114 occupies a large proportion of the head 110, which helps to reduce the weight of the head 110 and eliminates the need for sharp edges.

In addition, the sleeve 132 is configured such that, when inserted into the internal recess 114 of the femoral head 110, a base 141 of the sleeve 132 is level with the inner end 138 of the second edge 118. This further helps to eliminate steps or sharp edges in the design, which could catch on the psoas tendon.

An anterior-posterior plane X is illustrated in FIG. 4 which is perpendicular to the axis of the pole P and passes through the centre of curvature Y of the articulating surface 112. In this embodiment, the second edge 118 begins at an intersection Z between the anterior-posterior plane X and the articulating surface 112 (i.e. at a position which is 90 degrees from the pole P). Diametrically opposite to the intersection Z, the articulating surface 112 crosses the anterior-posterior plane X such that the first edge 116 begins at a position which is more than 90 degrees from the pole (in this case, approximately 120 degrees).

Furthermore, the second edge 118 has a radius of curvature which is less than that of the articulating surface 112 so as to eliminate the sharp edge commonly provided on a large femoral head prosthesis in an anterior and antero-inferior location. At the opposite side of the head 110, the first edge 116 is approximately parallel to the anterior-posterior plane X.

It will be clear from the above embodiments that the various aspects of the present invention provide a femoral head which has a reduced anterior and/or antero-inferior aspect in order to minimise the risk of groin pain caused by sharp edges catching on the psoas tendon. Advantageously, embodiments of the invention may comprise large metal femoral heads without the disadvantages associated with prior art designs. In addition, the relative position of the head on the stem can be adjusted without introducing steps or sharp edges which can catch on the psoas tendon, by employing sleeves which have an outer diameter configured such that the sleeve base is always level the end of the second edge and an inner surface which is varied in order to engage with a femoral neck at different positions therein.

It will be appreciated by persons skilled in the art that various modifications may be made to the above embodiments without departing from the scope of the present invention.

The invention claimed is:

1. A femoral head prosthesis comprising:
   an articulating surface which is more than hemi-spherical;
   an internal recess having a longitudinal axis defining a pole of the articulating surface, the longitudinal axis passing through the centre of curvature of the articulating surface; and
   a first edge which constitutes a posterior edge in use, and a second edge which constitutes at least one of an anterior edge or an antero-inferior edge in use,
   wherein (i) the first edge is further from the pole than the second edge, and (ii) the second edge comprises an arcuate portion having a radius of curvature which is less than that of the articulating surface.

2. The femoral head prosthesis according to claim 1 wherein the first edge is parallel to the anterior-posterior plane.

3. The femoral head prosthesis according to claim 1 wherein the first and second edges are joined by at least one intermediate edge.

4. The femoral head prosthesis according to claim 3 wherein the first and second edges are joined by two diametrically opposed intermediate edges.

5. The femoral head prosthesis according to claim 1 wherein the recess terminates at an inner end of the second edge and an inner end of the first edge.

6. The femoral head prosthesis according to claim 1 which is symmetrical about a plane which comprises the pole and which extends along an anterior-posterior direction.

7. The femoral head prosthesis according to claim 1 having an outer diameter in the range of 38 mm to 58 mm.

8. A femoral head prosthesis comprising:
   an articulating surface which is more than hemi-spherical;
   an internal recess having a longitudinal axis defining a pole of the articulating surface, the longitudinal axis passing through the centre of curvature of the articulating surface; and
   a first edge which constitutes a posterior edge in use, and a second edge which constitutes at least one of an anterior edge or an antero-inferior edge in use, wherein (i) the first edge is further from the pole than the second edge, (ii) an anterior-posterior plane is defined which is perpendicular to the axis of the pole that passes through the centre of curvature of the articulating surface, and (iii) the second edge has an outer end at an intersection between the anterior-posterior plane and the articulating surface, and wherein the second edge comprises an arcuate portion having a radius of curvature which is less than that of the articulating surface and wherein a tangent to the arcuate portion is perpendicular to the anterior-posterior plane at the outer end of the second edge and/or wherein the second edge comprises an inner end wherein a tangent to the arcuate portion is parallel to the anterior-posterior plane.

9. A femoral prosthesis comprising:

a femoral head comprising (i) an articulating surface which is more than hemi-spherical and which has a radius of curvature which extends beyond 180 degrees, (ii) an internal recess having a longitudinal axis defining a pole of the articulating surface, the longitudinal axis passing through the centre of curvature of the articulating surface, (iii) and a first edge which constitutes a posterior edge in use, and a second edge which constitutes at least one of an anterior edge or an antero-inferior edge in use, and wherein (a) the first edge is further from the pole than the second edge, and (b) the second edge comprises an arcuate portion having a radius of curvature which is less than that of the articulating surface; and one or more of a femoral stem prosthesis or a sleeve for a femoral neck.

10. The femoral prosthesis according to claim 9 wherein the femoral prosthesis comprises the sleeve, the sleeve being configured such that, when inserted into the internal recess of the femoral head, a base of the sleeve is level with an inner end of the second edge.

11. The femoral prosthesis according to claim 9 wherein the sleeve comprises a generally frusto-conical annulus having an inner surface configured for mating with a co-operating end of a femoral neck of a femoral stem prosthesis.

12. The femoral prosthesis according to claim 11 wherein the inner surface of the sleeve is offset with respect to the centre of the sleeve so that the central axis of the sleeve is not coincident with the central axis of the co-operating end of the femoral neck.

13. A femoral implant comprising:

a femoral stem and a femoral head;

the femoral head comprising an articulating surface which is more than hemi-spherical and which has a radius of curvature which extends beyond 180 degrees;

the femoral stem comprising a neck having a longitudinal axis defining a pole of the articulating surface of the femoral head, the longitudinal axis passing through the centre of curvature of the articulating surface;

the femoral head having a first edge which constitutes a posterior edge in use, and a second edge which constitutes an anterior edge and/or an antero-inferior edge in use;

wherein the first edge is further from the pole than the second edge; and the second edge comprises an arcuate portion having a radius of curvature which is less than that of the articulating surface.

14. The femoral implant according to claim 13 configured as a one-piece component having an integral femoral head and femoral stem.

15. A femoral prosthesis comprising:

a femoral head comprising (i) an articulating surface which is more than hemi-spherical, (ii) an internal recess having a longitudinal axis defining a pole of the articulating surface, the longitudinal axis passing through the centre of curvature of the articulating surface, (iii) and a first edge which constitutes a posterior edge in use, and a second edge which constitutes at least one of an anterior edge or an antero-inferior edge in use, and wherein the first edge is further from the pole than the second edge; and one or more of a femoral stem prosthesis or a sleeve for a femoral neck, wherein a plurality of different sleeves are provided, each sleeve being configured such that, when inserted into the internal recess of the femoral head, a base of the sleeve is level with an inner end of the second edge and wherein the inner surface of each sleeve is different so that each sleeve engages with the end of a femoral neck at varying positions therewithin.

\* \* \* \* \*